United States Patent [19]

Babbitt et al.

[11] 4,403,611

[45] Sep. 13, 1983

[54] SINUS EVACUATOR APPARATUS

[76] Inventors: Gerald J. Babbitt, 2424 N. Custis Rd., Arlington, Va. 22201; Ahmet Kasap, 3306 Wyndale Ct., Woodbridge, Va. 22192

[21] Appl. No.: 169,684

[22] Filed: Jul. 17, 1980

[51] Int. Cl.³ .............................................. A61M 1/00
[52] U.S. Cl. ....................................... 604/73; 604/94; 604/118; 604/173
[58] Field of Search ....................... 433/91, 92, 95, 96; 128/276, 277, 278, 297, 298, 299, 300, 239, 241; 15/352; 55/242

[56] References Cited

U.S. PATENT DOCUMENTS

| | | | |
|---|---|---|---|
| 1,209,846 | 12/1916 | Kells | 128/278 |
| 1,751,507 | 3/1930 | Brunette | 128/241 |
| 2,280,992 | 4/1942 | Wright et al. | 128/276 |
| 2,511,973 | 6/1950 | Sierra, Jr. | 128/276 |
| 3,267,510 | 8/1966 | Cote | 128/276 |

FOREIGN PATENT DOCUMENTS 791510 3/1958 United Kingdom .................. 55/242

OTHER PUBLICATIONS

The Merck Index, Windholz et al., Merck & Co., Rahway, N.J., 1976, 7441, p. 993.

Primary Examiner—Richard J. Apley
Assistant Examiner—J. L. Kruter
Attorney, Agent, or Firm—Neil F. Markva

[57] ABSTRACT

A portable, self-cleaning or flushing evacuator apparatus aspirates and removes sinus fluids from nasal and sinus cavities. The apparatus includes a housing having a vacuum producing compartment, a mucus collecting compartment, a sterilizing compartment and a storage compartment. A suction pervious barrier separates the mucus collecting compartment from the vacuum producing compartment. A rotatable propeller is mounted to a drive motor and located in the vacuum producing compartment. The propeller is effective to produce only a suction to draw through a catheter which is inserted into a nasal opening at one end and connected to the mucus collecting compartment at the other end thereof. The vacuum producing propeller is effective to produce an amount of suction sufficient to withdraw mucus material from the sinus cavities without causing irritation of the soft nasal tissues.

17 Claims, 10 Drawing Figures

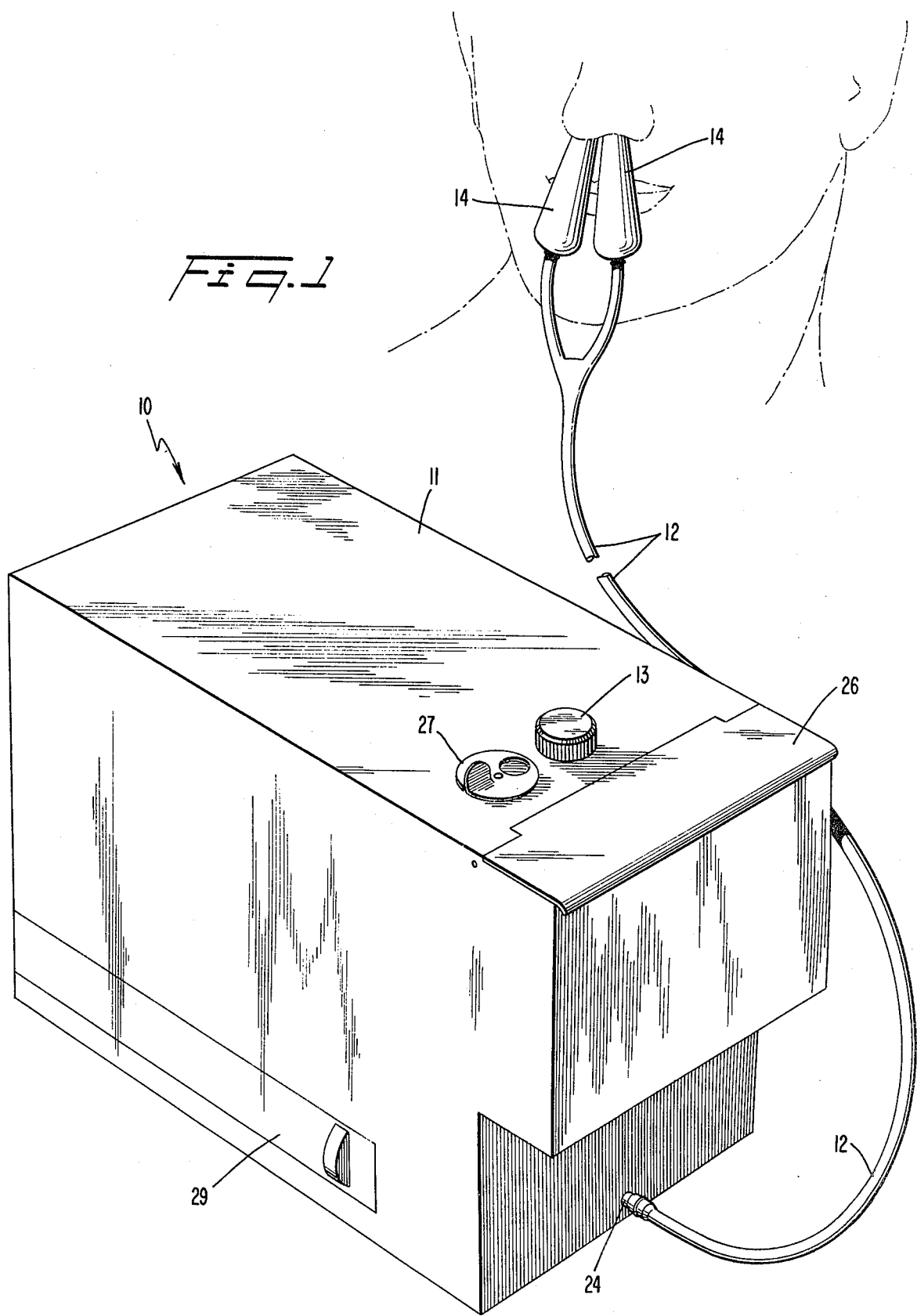

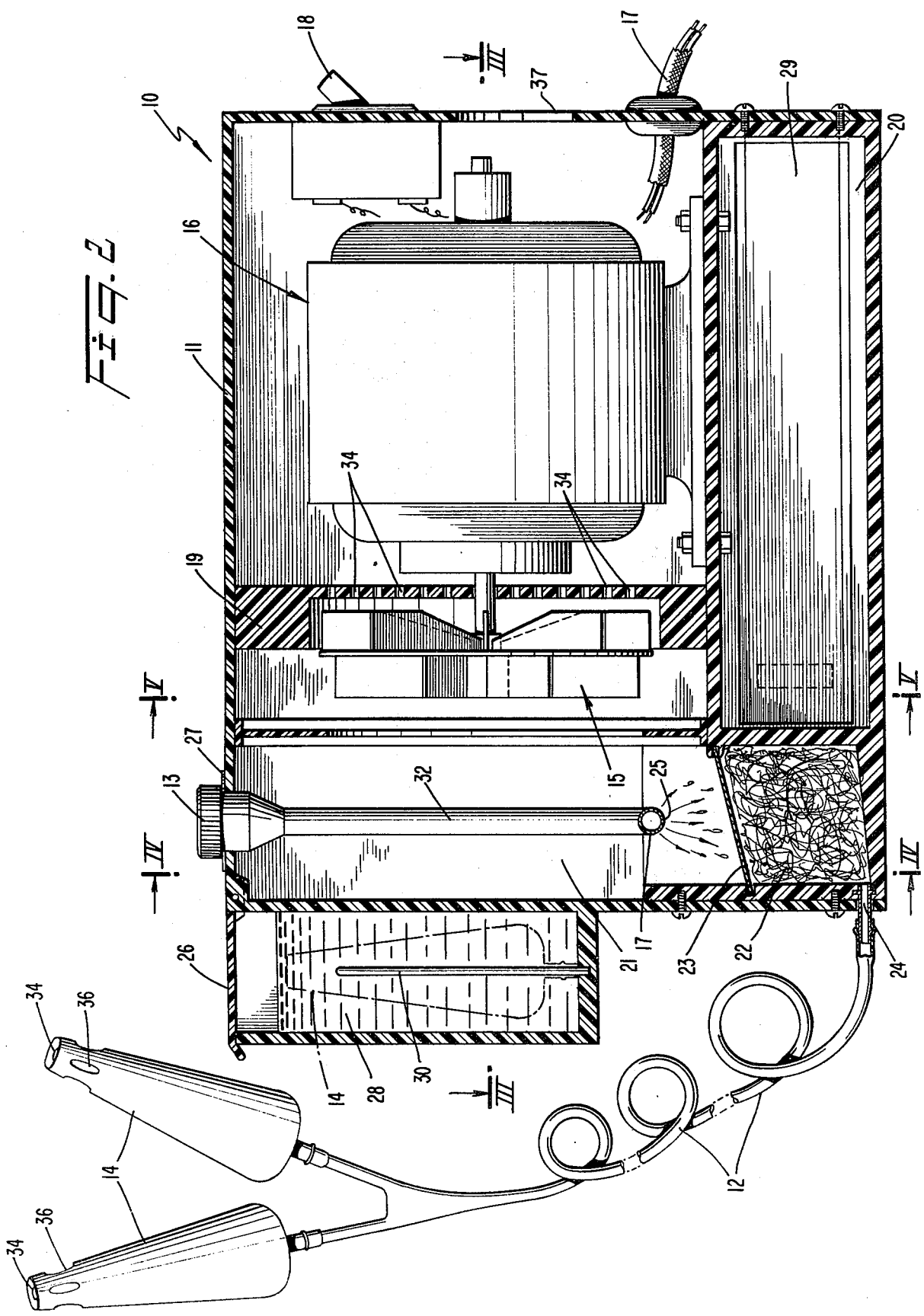

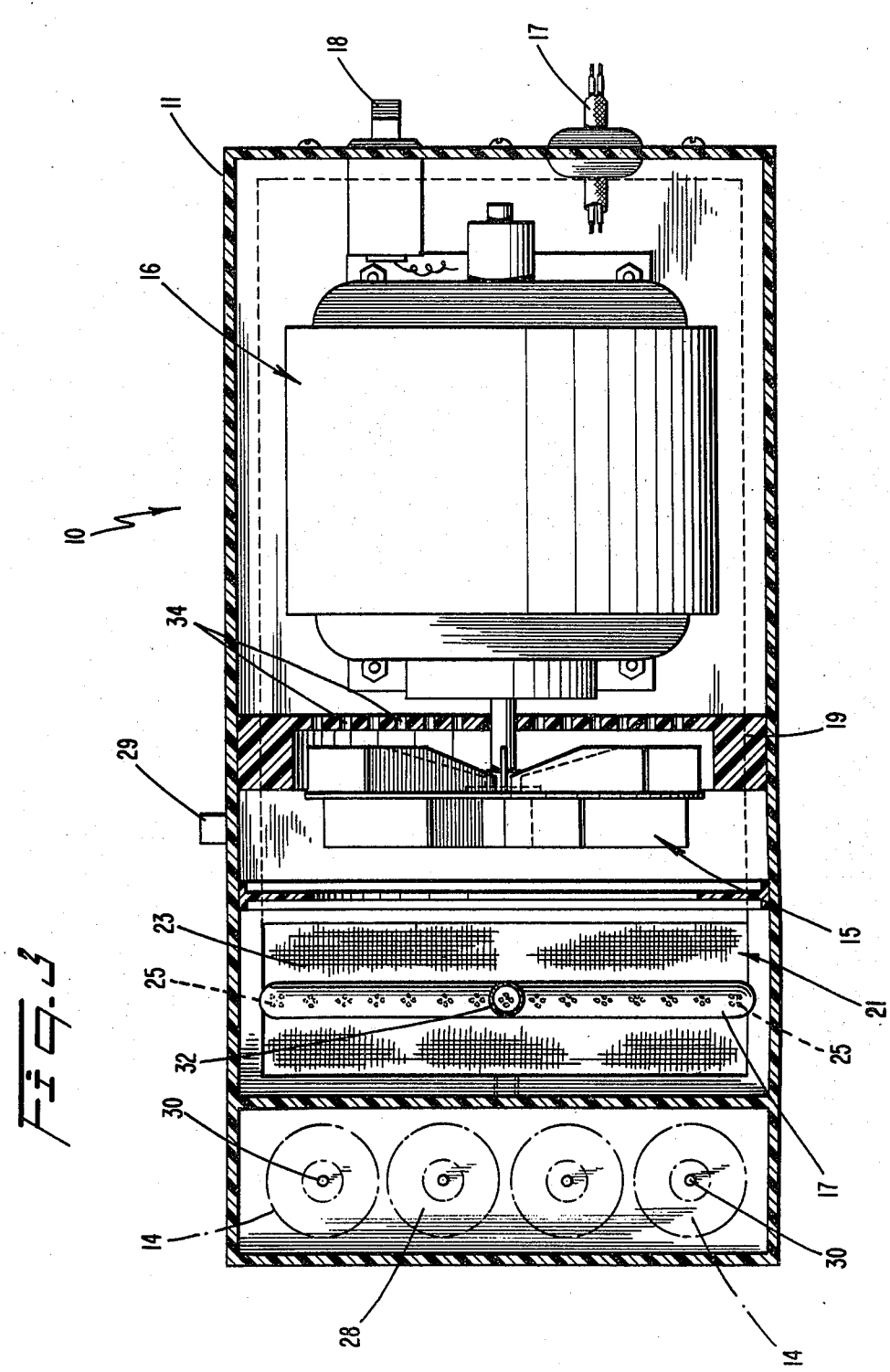

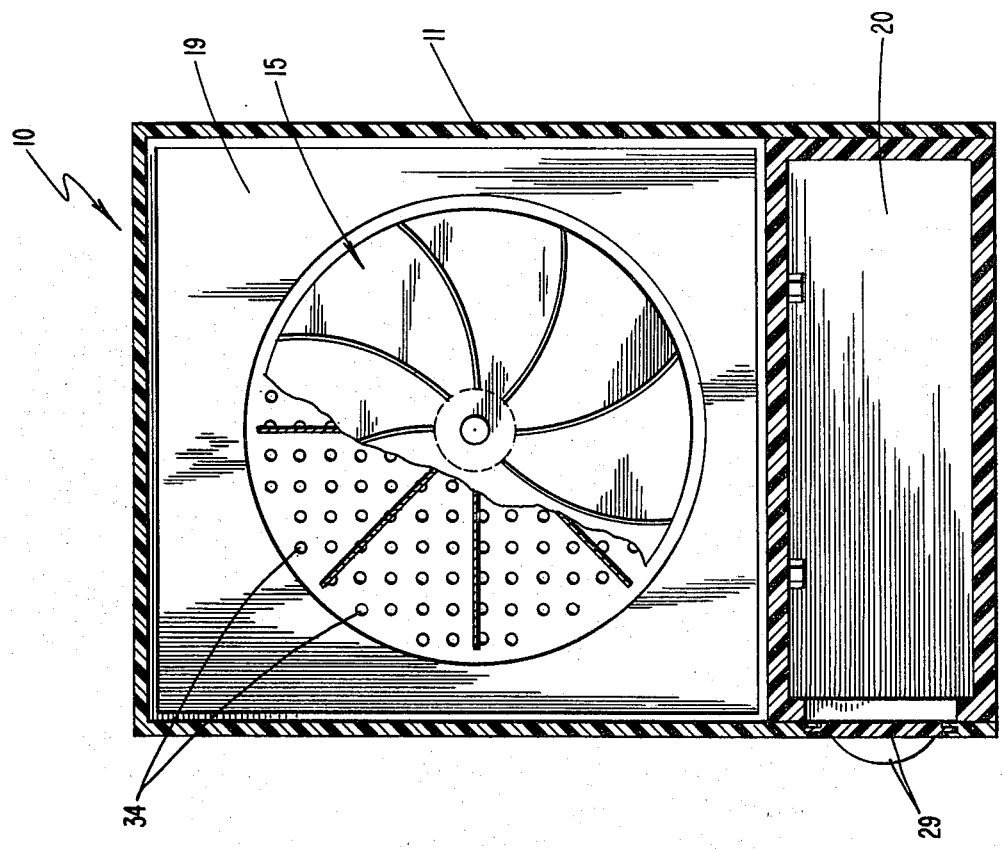
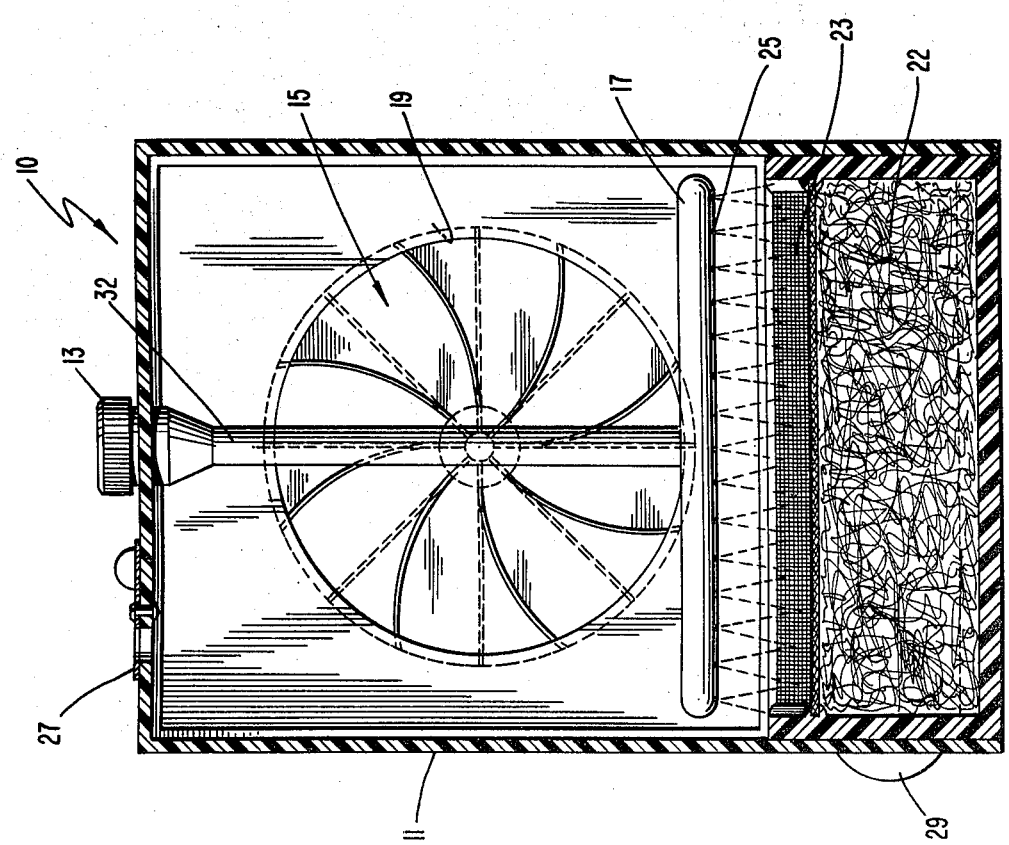

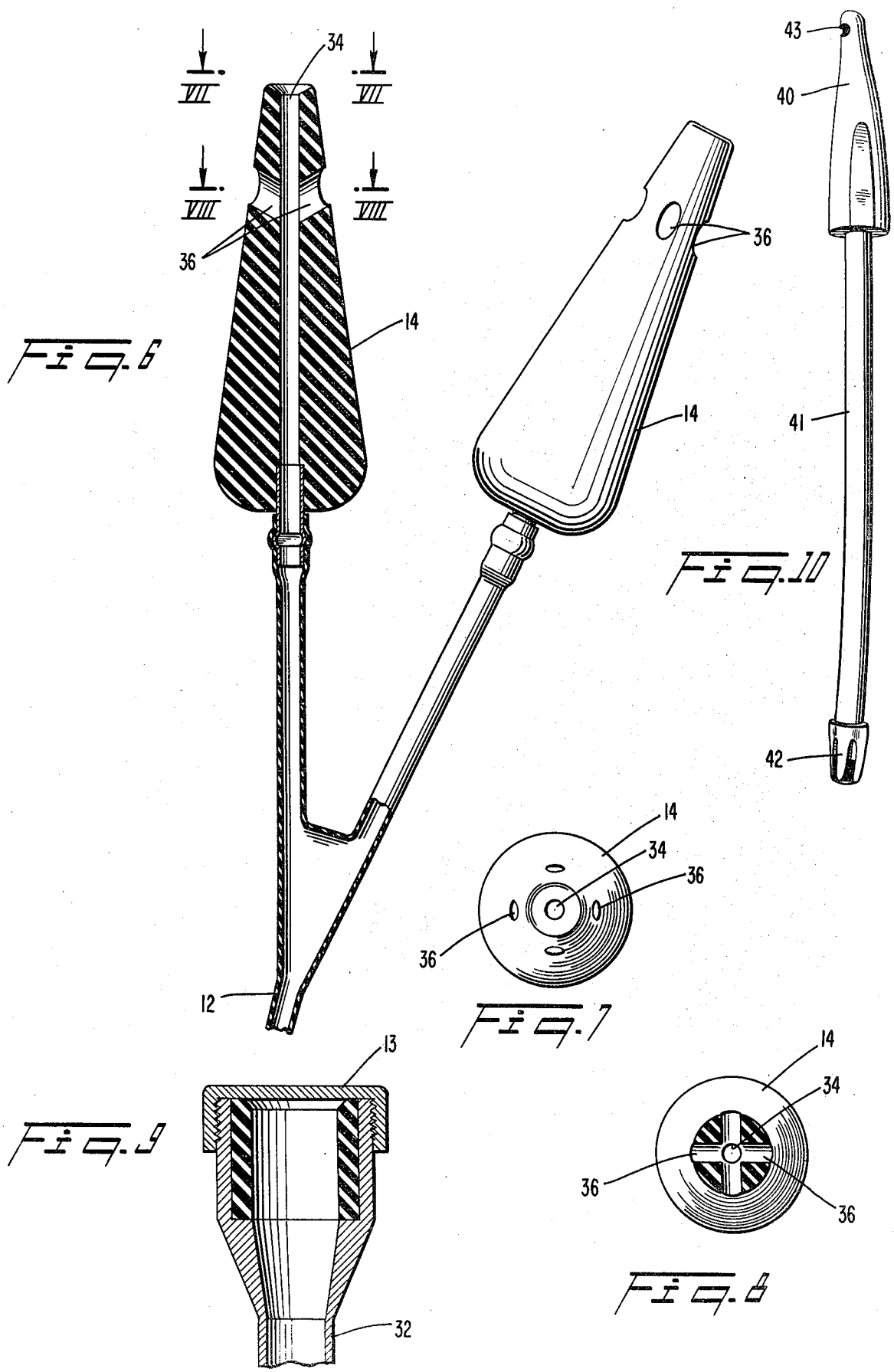

SINUS EVACUATOR APPARATUS

FIELD OF INVENTION

This invention relates to an apparatus which aspirates and removes mucus from nasal and sinus cavities. More specifically, the invention relates to a portable, self-cleaning or flushable evacuator apparatus to withdraw material from the sinuses without irritating nasal tissue.

BACKGROUND OF THE INVENTION

The maxillary sinus has a poor drainage system that requires the ciliary transport system to work against gravity. Ciliary activity is slowed or stopped by alternations in temperature, bacterial toxins and other factors such as changes in the pH. The maxillary sinus becomes infected very easily and is the most difficult to clear because all the other paranasal sinuses are capable of gravity drainage. However, the maxillary sinus opening is located high in the nasal sinus above the level of the middle turbinate. Consequently, the maxillary sinus does not cleanse well easily.

Increased mucus concentration causes a congestion in the nostrils, sinus cavities and eardrums, thereby leading to painful headaches. Sinus fluids which drain by gravity tend to cause irritation to the throat because of such drainage. When excessive mucus is produced because of infection or weather conditions, there is much discomfort, thereby affecting a person's daily performance.

Attempts to solve the problem associated with congestion include medication and evacuator devices. Medication generally gives only temporary relief at significantly high cost and sometime with various side effects. Known evacuator devices are operated only in physicians' offices where treatment requires not only time but also a significantly large medical bill. That is, while the known evacuator devices are reliable and efficient, their use is inconvenient and expensive.

There are various prior art devices constituting attempts to provide a portable and efficiently operating sinus cavity aspiration device. The U.S. Pat. No. 3,833,001 discloses a portable demucosant which requires large amounts of water to operate a Venture tube for creating the necessary suction to drain the nasal and maxillary sinuses. Thus, this prior art device is sufficient and is necessarily dependent upon the use of large amounts of water.

Other prior art devices are shown in U.S. Pat. Nos. 1,481,008, 2,078,180, 2,280,992 and 3,502,078. These include disclosures of flexible bulbs to provide intermittent vacuum pulses to relieve the mucus. These are generally inefficient and unsanitary. Other types of devices disclosed in these references are generally large and bulky and not suitable for home use.

PURPOSE OF THE INVENTION

The primary object of this invention is to provide a portable, self-cleaning or flushable evacuator apparatus which may be used at home and effect the drainage of the nasal and maxillary sinuses without damage to the nasal tissues.

Another object of the invention is to provide an evacuator apparatus for aspirating fluid materials from the nasal and sinus cavities while providing a sterilizing, cleaning and storage function when the apparatus is not in use.

A still further object of this invention is to provide an efficient, portable evacuator apparatus to provide a variable continuous suction available for periodic use to keep nasal and sinus cavities clear of mucus material.

SUMMARY OF THE INVENTION

The evacuator appartus as disclosed herein comprises a housing means including a vacuum producing portion and a mucus collecting portion. Propeller means is rotatably mounted to a drive motor in the vacuum producing portion. Catheter means is connected to the mucus collecting portion and is effective for insertion into a nasal opening. The propeller means is effective to produce only a suction to draw through the catheter means when the catheter means is inserted into a nasal opening. Propeller means is effective to produce an amount of suction sufficient to withdraw mucus material from the sinus cavities without causing irritation of the soft nasal tissues.

Another feature of the invention provides a suction previous barrier disposed to separate the vacuum producing portion and the mucus collecting portion. The pervious barrier is effective to allow suction to be drawn through the catheter means while preventing mucus from entering the vacuum producing portion.

The use of a single container as the housing means constitutes a significant feature of the present invention. A single container has a vacuum producing compartment, a mucus collecting compartment, a sterilizing compartment and a storage compartment. A flushing mechanism is provided to impinge a liquid jet against the suction pervious barrier separating the mucus collecting compartment from the vacuum producing compartment. The propeller is rotatably mounted in the vacuum producing compartment. A catheter is connected to the mucus collecting compartment while the apparatus is in use and is stored in the sterilizing compartment when not in use. The hose for the catheter is placed in the storage compartment when the device is not in use.

BRIEF DESCRIPTION OF DRAWINGS

Other objects of this invention will appear in the following description and appended claims, reference being made to the accompanying drawings forming a part of the specification wherein like reference characters designate corresponding parts in the several views.

FIG. 1 is a perspective view of the apparatus made in accordance with this invention during use;

FIG. 2 is a sectional view of the housing showing the vacuum producing mechanism, flushing means and catheter means in place within the housing;

FIG. 3 is a sectional view along line III—III of FIG. 2;

FIG. 4 is a sectional view along line IV—IV of FIG. 2;

FIG. 5 is a sectional view along line V—V of FIG. 2;

FIG. 6 is a fragmentary view, partly in section, of a catheter made in accordance with this invention;

FIG. 7 is a view of the catheter along line VII—VII of FIG. 6;

FIG. 8 is a sectional view along line VIII—VIII of FIG. 6;

FIG. 9 is a fragmentary sectional view of the coupling and of the flushing means made in accordance with this invention;

FIG. 10 is an elevational view of a catheter member which may be used in accordance with this invention.

DETAILED DESCRIPTION

The evaporator apparatus, generally designated 10, is shown in use in FIG. 1 for aspirating the sinus fluids from the nasal passages. A propeller 15 is rotatably mounted to a drive motor 16 and is disposed within a vacuum producing portion or compartment of the housing 11. Drive motor 16 operates on standard household voltage and includes an on-off switch 18 being electrically connected via cord 17. Suction wall 19 includes a plurality of openings 34 through which air is drawn from the front of propeller 15 to the rear thereof. Air is then exhausted through an opening 37 in the housing 11 at the rear thereof.

During use, negative pressure is created in chamber 21. A mucus collecting chamber 22 is separated from the suction producing chamber 21 by a metal mesh screen 23 constituting a suction pervious barrier. Screen 23 is effective to allow suction to be drawn through the catheter members 14 while preventing mucus from entering the vacuum producing chamber 21. Catheter members 14 are connected to mucus collecting chamber 22 via tube 12 and coupling connector 24.

The self-cleaning or flushing mechanism of the apparatus 10 includes a vertically disposed tube having an inverted T-shape. The tube includes a vertical section 32 and a horizontally disposed section 17. A cap 13 is placed on the open end of the vertical section 32 for maintaining suction within the housing 11 while the evacuator apparatus is in use as shown in FIG. 1. Once the evacuating procedure is complete, cap 13 is removed and a liquid cleaning fluid such as tap water is injected into the flushing system. The horizontal section includes a plurality of openings which direct jets of water against the upper portion of the screen 23 to effect cleaning thereof. Thus, the fine filter mesh screen must be water resistant and capable of holding any mucus material within the chamber 22 while the evacuation procedure is being effected.

A suitable flexible tube may be connected between the standard home faucet and the open end of the vertical tube 32. Thus water is transferred under pressure to the vertical tube 32 and out openings 25 of the horizontal section 17. Contaminated liquid is discharged out the coupling connection 24 when tube 12 is not connected thereto. The bottom wall of compartment 22 is angled with respect to the horizontal to aid in the discharge of all contaminated liquid.

A sterilizing compartment 28 is shown filled with sterilizing liquid and formed within housing 11. A hinged top 26 covers the sterilizing liquid. A plurality of vertically disposed rods 30 are used to support the catheter members 14 after their use.

Catheter members 14 include a nose insert portion having a conical outer shape effective to support the nasal membrane when inserted in the nasal opening. The nose insert portion includes a central aperture 34 at the end of a center bore as shown. A plurality of apertures 36 are angularly disposed with respect to the central bore and located around the outer periphery of the nose insert portion. The lateral openings 36 are equiangularly disposed around the circumference of the catheter members 14. The angular disposition of the openings 36 provides better collection for sinus fluids into the central bore of the catheter members 14. The conical shape of the nose insert portion of members 14 provides a support surface for the nasal membranes, preventing any danger of membrane collapse or injury during the aspiration process. Either one or both of the catheter members may be used as desired. Any open tube could be used to adjust the amount of negative pressure through the opening and closing of same with a finger.

The catheter members 14 may be made of any non-toxic, flexible plastic material such as polyvinyl chloride, polyethylene, nylon or the like. Flexible tube 12 may also be made of flexible plastic material. A single catheter member as shown in FIG. 10 may be used instead of two as in the earlier embodiment and includes a nose insert 40 having openings 43. Nose insert 40 is at one end of a transparent portion 41 and a mucus strainer 42 is located at the other end thereof. A suction hose is disposed over the mucus strainer 42 when in operation. The type of mucus strainer 42 is well known.

A storage compartment 20 is located within the lower portion of housing 11. A sliding door 29 covers the storage compartment. When not being used, the flexible tube 12 is disposed within the storage compartment 30. The entire unit as disclosed herein is compact and simple to operate for home use.

The drive motor 16 may be a variable speed or fixed speed motor. An adjustable vacuum control valve 27 on housing 11 may be opened to the atmosphere at any desired position to control the amount of vacuum in the compartment 21. The drive motor 16 may operate at 3,450 rpm and be capable of moving 10 cubic feet of air per minute to create a vacuum in the range of about 5 to 15 mm mercury which inherently establishes vacuum conditions in the mucus collection chamber 22. Thus, while there are vacuum conditions in the mucus collection chamber 22, the maximum vacuum created will not cause irritation of the soft nasal tissues.

Any suitable tube may be used to deliver pressurized water from the standard water faucet to the vertical tube sections 32. The water flows downwardly and streams out the orifice 25 and horizontal section 17 to clean the collecting chamber 22 and the filter mesh screen 23. Housing 11 may be made of any lightweight, strong plastic material of a suitable type.

While the Sinus Evacuator Apparatus has been shown and described in detail, it is obvious that this invention is not to be considered as being limited to the exact form disclosed, and that changes in detail and construction may be made therein within the scope of the invention, without departing from the spirit thereof.

Having thus set forth and disclosed the nature of this invention, what is claimed is:

1. A portable, flushable evacuator apparatus for aspiration of material from sinus cavities, said apparatus comprising:
    (a) housing means including therein a vacuum producing portion a mucus collection portion fixedly juxtaposed to one another and a means for flushing the mucus collecting portion with a cleansing fluid medium,
    (b) propeller means rotatably mounted to a drive motor in the vacuum producing portion,
    (c) catheter means connected to the mucus collection portion and being effective for insertion into a nasal opening,
    (d) said propeller means being effective to produce only a suction to draw through the catheter means when said catheter means is inserted into a nasal opening,
    (e) said propeller means being effective to produce an amount of suction sufficient to withdraw mucus material from the sinus cavities without causing irritation of the soft nasal tissues, (f) said mucus collection portion having a mucus collecting compartment and a suction pervious barrier means that separates the mucus collection compartment from the vacuum producing portion and is flushable with the cleansing fluid medium to remove any mucus collected therein (g) said barrier being effective to allow suction to be drawn through the catheter means while preventing mucus from entering the vacuum producing portion, and (h) said flushing means being closable while said propeller means is producing a suction in said mucus collecting portion.

2. An apparatus as defined in claim 1 wherein said propeller means produces either a steady or a variable suction.

3. An apparatus as defined in claim 1 wherein said catheter means includes a nose insert portion having a conical outer shape effective to support the nasal membrane when inserted in the nasal opening.

4. An apparatus as defined in claim 3 wherein said nose insert portion includes a central aperture at the end of a center bore and a plurality of apertures angularly disposed with respect to the central bore and located around the outer periphery of the nose insert portion.

5. An apparatus as defined in claim 3 wherein said nose insert portion includes four apertures equi-angularly disposed around the circumference of said catheter means.

6. An apparatus as defined in claim 1 wherein said flushing means includes nozzle means having openings at one end directed toward the suction pervious barrier and being connectable to a cleaning fluid source at the other end thereof.

7. An apparatus as defined in claim 6 wherein said nozzle means includes a T-shaped tube disposed with the T in an inverted position providing a horizontal section and a vertical section, said nozzle openings being located along the length of the horizontal section.

8. An apparatus as defined in claim 6 wherein the nozzle means is connectable to a standard home water faucet.

9. An apparatus as defined in claim 1 wherein said housing means includes a sterilizing portion for containing the catheter means which are not in use.

10. An apparatus as defined in claim 9 wherein said sterilizing portion is defined by a separate compartment in the housing means with said compartment being effective to contain a sterilization material.

11. An apparatus as defined in claim 10 wherein said sterilizing material is liquid.

12. An apparatus as defined in claim 1 wherein the housing means includes a catheter hose storage compartment.

13. An apparatus as defined in claim 1 wherein said housing means includes a means for controlling the amount of suction being pulled through the catheter means.

14. A portable, flushable evacuator apparatus for aspiration of material from sinus cavities, said apparatus comprising:

(a) housing meas including a single container having a vacuum producing compartment, a mucus collecting compartment, a sterilizing compartment, and a storage compartment, (b) a suction pervious barrier separates the mucus collecting compartment from the vacuum producing compartment, (c) propeller means rotatably mounted to a drive motor in the vcuum producing portion, (d) catheter means connected to the mucus collection portion and being effective for insertion into a nasal opening, (e) said propeller means being effective to produce only a suction to draw through the catheter means when said catheter means is inserted into a nasal opening, (f) said propeller means being effective to produce an amount of suction sufficient to withdraw mucus material from the sinus cavities without causing irritation of the soft nasal tissues, (g) flushing means is connected to the housing and is effective to direct a stream of cleaning fluid against the suction pervious barrier to effect cleaning of the mucus collecting compartment.

15. An apparatus as defined in claim 14 wherein said housing means includes a means for controlling the amount of suction being pulled through the catheter means.

16. An apparatus as defined in claim 14 wherein said mucus collecting compartment includes at least one opening therein to be coupled to a cathether hose in fluid communication.

17. An apparatus as defined in claim 16 wherein said cathether hose is removably coupled to said opening, and
the coupling is terminated during flushing operation of said mucus collection compartment.

* * * * *